(12) United States Patent
Cinader, Jr. et al.

(10) Patent No.: US 8,875,873 B2
(45) Date of Patent: Nov. 4, 2014

(54) PACKAGED ORTHODONTIC ASSEMBLY WITH RETAINING MEMBER

(75) Inventors: David K. Cinader, Jr., Walnut, CA (US); Alan F. Conley, Fullerton, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/699,754

(22) PCT Filed: May 25, 2011

(86) PCT No.: PCT/US2011/037924
§ 371 (c)(1),
(2), (4) Date: Nov. 26, 2012

(87) PCT Pub. No.: WO2011/153039
PCT Pub. Date: Dec. 8, 2011

(65) Prior Publication Data
US 2013/0075282 A1   Mar. 28, 2013

Related U.S. Application Data (60) Provisional application No. 61/350,634, filed on Jun. 2, 2010.

(51) Int. Cl.
| | |
|---|---|
| A61B 19/02 | (2006.01) |
| A61C 19/02 | (2006.01) |
| B65B 5/04 | (2006.01) |
| A61C 7/14 | (2006.01) |

(52) U.S. Cl.
CPC . *A61C 19/02* (2013.01); *B65B 5/04* (2013.01); *A61C 2202/00* (2013.01); *A61C 7/14* (2013.01)
USPC .......... 206/63.5; 206/368; 206/369; 206/462; 206/469; 433/8; 433/9; 433/10; 433/11; 433/24

(58) Field of Classification Search
CPC .......... A61C 19/10; A61C 19/02; A61C 7/12; A61C 2202/01; B65D 81/022
USPC ......... 206/368, 369, 461, 462, 469, 813, 438, 206/460, 0.82, 588, 63.5, 5.1, 751, 752, 206/756, 292–298, 784, 754, 722, 709, 711, 206/714, 716; 433/3, 8–17, 24; 215/344, 215/343, 341, 346; 220/806, 796; 53/471
See application file for complete search history.

(56) References Cited

U.S. PATENT DOCUMENTS 3,918,581 A * 11/1975 Scammon et al. ............ 206/722
4,076,872 A    2/1978 Lewicki
(Continued)

FOREIGN PATENT DOCUMENTS

EP      2272459        1/2011
JP      01-23947 A     1/1989
(Continued)

OTHER PUBLICATIONS

International Search Report PCT/US2011/037924 Aug. 22, 2011, 4 pgs.

*Primary Examiner* — Andrew Perreault
*Assistant Examiner* — James M Van Buskirk
(74) *Attorney, Agent, or Firm* — Kevin W. Weber (57) ABSTRACT

Orthodontic assemblies and related methods are provided where an adhesive coated orthodontic appliance is received in a container that includes a substrate and a lid having a retaining member. When the lid is closed, the retaining member is complemental to the shape of the appliance and engages with the appliance. By conforming to the shape of the appliance, the retaining member constrains the appliance from shifting in lateral and vertical directions within the container. When the lid is opened, the associated retaining member disengages from the appliance, thereby facilitating user access to the appliance.

20 Claims, 4 Drawing Sheets

(56) References Cited

U.S. PATENT DOCUMENTS

| | | | |
|---|---|---|---|
| 4,978,007 A | 12/1990 | Jacobs | |
| 5,015,180 A | 5/1991 | Randklev | |
| 5,172,809 A * | 12/1992 | Jacobs et al. | 206/368 |
| 5,183,403 A * | 2/1993 | Masuhara et al. | 433/9 |
| 5,328,363 A | 7/1994 | Chester | |
| 5,429,229 A | 7/1995 | Chester | |
| 5,538,129 A * | 7/1996 | Chester et al. | 206/63.5 |
| 5,575,645 A | 11/1996 | Jacobs | |
| 5,827,058 A | 10/1998 | Kelly | |
| 6,089,861 A | 7/2000 | Kelly | |
| 6,183,249 B1 | 2/2001 | Brennan | |
| 6,364,098 B2 * | 4/2002 | Yavitz | 206/5.1 |
| 6,880,706 B2 * | 4/2005 | Braconnot et al. | 206/583 |
| 6,960,079 B2 | 11/2005 | Brennan | |
| 7,264,117 B2 * | 9/2007 | Atkin et al. | 206/369 |
| 7,726,470 B2 * | 6/2010 | Cinader et al. | 206/63.5 |
| 2003/0196914 A1 | 10/2003 | Tzou | |
| 2008/0096150 A1 | 4/2008 | Cinader, Jr. | |
| 2008/0286710 A1 | 11/2008 | Cinader, Jr. | |
| 2009/0233252 A1 | 9/2009 | Cinader, Jr. | |

FOREIGN PATENT DOCUMENTS

| | | |
|---|---|---|
| JP | 8140994 | 6/1996 |
| JP | 2001-318733 A | 11/2001 |
| WO | WO 2006/058162 | 6/2006 |
| WO | WO 2008/144123 | 11/2008 |
| WO | WO 2010/126716 | 11/2010 |

* cited by examiner

PACKAGED ORTHODONTIC ASSEMBLY WITH RETAINING MEMBER

1. FIELD OF THE INVENTION

Provided are packaged assemblies for orthodontic appliances. More particularly, packaged assemblies are provided for orthodontic appliances that are coated with an adhesive for facilitating bonding of the appliances to a tooth structure.

2. DESCRIPTION OF THE RELATED ART

Orthodontics is a specialized area of dentistry concerned with the diagnosis and treatment of dental malocclusions to improve bite function, hygiene, and facial aesthetics. Orthodontic therapy commonly uses tiny appliances called brackets and molar tubes which are bonded to a patient's teeth. Brackets and molar tubes contain slots and passageways, respectively, to accommodate a resilient "U"-shaped wire called an orthodontic archwire. During treatment, the archwire is secured within the slots and passageways of the brackets and molar tubes. While the archwire is initially distorted, it gradually returns to its original shape over the course of treatment, thereby applying therapeutic forces to urge the malpositioned teeth to proper locations.

Brackets, molar tubes, and other bondable appliances are generally affixed to teeth using a suitable orthodontic adhesive. Traditionally, adhesives were painstakingly applied, one at a time, to each appliance by an orthodontic assistant at the orthodontic office. Since this can be a tedious process, manufacturers have provided appliances that are coated in advance, or "pre-coated," at the factory to save time for the orthodontist. Coated appliance configurations are described in detail in issued U.S. Pat. No. 4,978,007 (Jacobs, et al.), U.S. Pat. No. 5,015,180 (Randklev), and U.S. Pat. No. 5,328,363 (Chester et al.).

Pre-coated brackets and molar tubes provide a significant advantage to the practitioner. First, these appliances provide for a high degree of precision in the amount of adhesive that is dispensed on the base of each appliance compared with hand-coating appliances. Second, these appliances are easy to use and save time, since a practitioner can conveniently remove a bracket from its respective container and place it directly on the patient's tooth without need for intervening steps. Typically, the adhesive is a light curable adhesive which allows the appliance, once placed on the tooth surface, to be carefully positioned in a proper orientation before a curing lamp is activated to cure the adhesive and securely fix the appliance in place.

Various approaches have been taken in packaging adhesive-coated orthodontic appliances. In one approach, the appliance and adhesive are placed in a sealed "blister" or similar disposable container. The adhesive is secured against a wall of the container having a suitable release surface such that the appliance and adhesive lift off together when the appliance is plucked from the container. This approach is described in, for example, issued U.S. Pat. No. 6,183,249 (Brennan, et al.). Another approach involves using mechanical structures to suspend the appliance in the container such that the adhesive does not contact any surfaces of the container. Examples of this approach are described in issued U.S. Pat. No. 5,827,058 (Kelly, et al.) and U.S. Pat. No. 6,089,861 (Kelly, et al.).

3. SUMMARY OF THE INVENTION

In packaging an adhesive coated orthodontic appliance, it can be challenging to provide ease of use in dispensing the appliance from the package while also ensuring that the appliance is properly secured during transportation and handling. These considerations often militate against one another. For example, placing support structure against all four sides of an appliance would securely hold the appliance, but such structure may be a nuisance when trying to extract the appliance from the container. On the other hand, a package with minimal support structure would allow easy access to the appliance, but also increases the risk that the appliance would be dislodged when the package is dropped or otherwise mishandled. Moreover, configurations having little or no support structure generally rely on the unhardened adhesive to secure the appliance in the container, thereby adding an engineering constraint to the adhesive formulation that would not otherwise be present.

As a solution, orthodontic assemblies and related methods are provided where an adhesive coated orthodontic appliance is received in a container that includes a substrate and a dual-purpose lid. The lid protectively seals the coated appliance in the container, and also has retaining structure that is at least partially complemental to the shape of the appliance and engages with the appliance when the lid is closed. By conforming to the shape of the appliance, the retaining structure constrains the appliance from shifting in lateral and vertical directions within the container. When the lid is opened, the associated retaining structure disengages from the appliance, allowing convenient user access.

Advantageously, these assemblies and methods enable the appliance to be held securely during shipping and handling. This protects the appliance and also preserves the integrity of the adhesive pad interposed between the substrate and base of the appliance. Moreover, because the retaining structure is conveniently withdrawn from the appliance immediately prior to use, there is an abundance of space along the periphery of the appliance to provide easy access using tweezers or other hand instruments. Finally, by bracing the appliance within the container, these assemblies alleviate the burden on the adhesive to support the appliance during transit, leading to greater freedom in engineering the composition of the adhesive.

In one aspect, a packaged orthodontic assembly is provided. The packaged orthodontic assembly comprises an orthodontic appliance having a base for attachment to a tooth surface; an adhesive extending across at least a portion of the base; a substrate having a release surface in contact with the adhesive; a lid coupled to the substrate and comprising a retaining member that contacts the appliance at a non-zero angle relative to the release surface to hinder relative sliding movement between the appliance and the release surface.

In another aspect, a method of packaging an orthodontic appliance is provided, comprising coating a base of the appliance with an orthodontic adhesive; placing the appliance on a substrate, wherein the adhesive contacts the substrate; and placing a lid over both the appliance and the substrate, wherein the lid comprises a retaining member that at least partially surrounds the appliance to hinder relative sliding movement between the appliance and the substrate.

4. BRIEF DESCRIPTION OF THE DRAWINGS

FIGS. 8b and 8c are fragmentary, cross-sectional plan views depicting two alternative embodiments of the assembly of FIG. 8a.

5. DETAILED DESCRIPTION OF THE PREFERRED EMBODIMENTS

Figure 1:
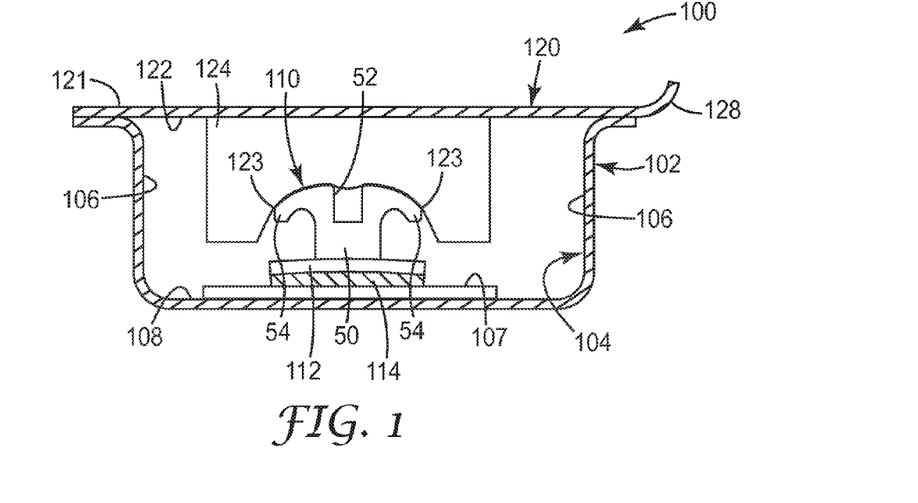
FIG. 1 is a side cross-sectional view of a packaged orthodontic assembly according to one embodiment.

A packaged orthodontic assembly according to one embodiment is illustrated in FIG. 1 and designated by the numeral 100. The assembly 100 includes a substrate 102 having a recess 104. The recess 104, in turn, has vertical surfaces 106 and a horizontal surface 108. The horizontal surface 108 further includes a release surface 107. As defined herein, a release surface 107 is a surface that is initially in contact with an adhesive and from which the adhesive may be subsequently removed. Preferably, the release surface 107 is a non-stick surface, such as provided by a low surface energy polymer coating, porous foam, or release liner such as a polyester film or fluorinated copolymer film. Further examples and aspects of release surfaces are described in issued U.S. Pat. No. 6,183,249 (Brennan, et al.).

Received in the recess 104 is an orthodontic appliance 110. As shown, the appliance 110 is an orthodontic bracket having a body 50, archwire slot 52, tiewings 54, and a bonding base 112 for attachment to a tooth surface of a patient. The appliance 110 need not be a bracket and may instead be any of a number of bondable orthodontic appliances, including buccal tubes, buttons, cleats and sheaths. Moreover, the appliance 110 may be suitable for attachment either to the labial or lingual surface of the patient's teeth. The appliance 110 is coated with an orthodontic adhesive 114 that extends over at least a portion of the base 112.

The orthodontic adhesive 114 may include any of a variety of bonding compositions known in the art. Preferably, the orthodontic adhesive 114 is a light curable adhesive that is hardenable by exposure to actinic radiation. Suitable adhesives include, for example, TRANSBOND XT brand Light Cure Adhesive and TRANSBOND PLUS brand Color Change Adhesive, both available from 3M Unitek. As another option, the adhesive 114 can be a compressible adhesive, as described in U.S. Patent Publication Nos. 2008/0096150 (Cinader) and 2009/0233252 (Cinader). Further aspects of adhesive pre-coated appliances are described in U.S. Pat. No. 5,575,645 (Jacobs, et al.) and U.S. Pat. No. 6,960,079 (Brennan et al.).

As shown in FIG. 1, the adhesive 114 contacts the release surface 107 of the substrate 102. In some embodiments, the release surface 107 allows the adhesive 114 to separate cleanly from the substrate 102 when the appliance 110 is lifted or peeled away from the substrate 102 without leaving any portion of the adhesive 114 on the substrate 102 and without unduly deforming the initial pillow-like shape of the adhesive 114. In other embodiments, a portion of the adhesive 114 is intentionally absorbed into, or otherwise retained on, the release surface 107 when the appliance 110 is lifted or peeled away from the substrate 102. This can be especially advantageous for compressible adhesives, where it may be desirable for the adhesive 114 to be maintained in a resin-saturated state.

A peelable lid 120, having a top surface 121 and a bottom surface 122, is coupled to the substrate 102 and extends over the appliance 110 and the recess 104. In the example shown, the lid 120 laminated to the substrate 102 by a releasable adhesive. However, a hinge or other type of coupling may also be used. When the lid 120 is in a closed configuration, as shown in FIG. 1, the appliance 110 is located between the substrate 102 and the lid 120. In some embodiments, the lid 120 contacts the substrate 102 along one or more locations that partially or fully surround the appliance 110, as viewed from directions perpendicular to the top and bottom surfaces 121,122 of the lid 120. In some embodiments, the lid 120 hermetically seals the appliance 110 within the recess 104 of the substrate 102.

The lid 120 may include both rigid and flexible components. In some embodiments, the lid 120 is releasably coupled to the substrate 102 and flexibly peeled away from the substrate 102. In other embodiments, the lid 120 is pivotally coupled to the substrate 102 and is opened using a hinge-type mechanism located at one side of the recess 104.

Assuming that the adhesive 114 is a light curable adhesive, both the substrate 102 and the lid 120 preferably block passage of light, particularly light having wavelengths that induce hardening of the adhesive 114. Optionally, either the lid 120 or the substrate 102 transmits light over a limited portion of the visible light spectrum such that the practitioner can visually ascertain whether or not the appliance 110 is situated in the recess 104 when the lid 120 is closed. Alternatively, the substrate 102 or the lid 120 may be constructed from a polymer composite that completely blocks passage of actinic radiation, as disclosed in U.S. Patent Publication No. 2003/0196914 (Tzou, et al.). In some embodiments, the substrate 102 and lid 120 also block passage of water vapor, oxygen, and other gases.

To facilitate opening of the lid, a portion of the lid 120 extends beyond a lateral edge of the substrate and acts as a handle that can be grasped between the thumb and forefinger of a user while peeling the lid 120 away from the substrate 102.

As shown in FIG. 1, the bottom surface 122 of the lid 120 (adjacent to the recess 104) and the release surface 107 of the substrate 102 are generally parallel with each other when the lid 120 is in its closed orientation. By contrast, the appliance 110 has certain surfaces 123 that contact the retaining member 124. The surfaces 123 are non-parallel with both the bottom surface 122 of the lid 120 and the release surface 107 of the substrate 102. In the embodiment shown in FIG. 1, the surfaces 123 are located on curved labial surfaces of the bracket tiewings.

A retaining member 124 extends outwardly from the bottom surface 122 of the lid 120 and contacts one or more surfaces 123 of the appliance 110 at a non-zero angle relative to the release surface 107 of the substrate 102. Preferably, and as shown, the retaining member 124 is at least somewhat flexible and has a surface contour that generally conforms to at least a portion of the labial-facing surfaces of the appliance 110. Advantageously, the retaining member constrains movement of the appliance 110 in both lateral and vertical directions.

First, by contacting the surfaces 123 of the appliance 110, the retaining member 124 effectively hinders relative sliding movement between the appliance 110 and the lid 120. Further, because the lid 120 and the substrate 102 are coupled to each other, the retaining member 124 also hinders relative sliding movement between the appliance 110 and the substrate 102. Preferably, the retaining member 124 partially surrounds the appliance 110 to prevent both rotation of the appliance 110 in the plane of the release surface 107 and lateral translation of the appliance 110 across the release surface 107. As used herein, "partially surrounding" the appliance indicates that interference can result from translating or rotating the appliance within the plane of the release surface.

Preferably, the retaining member 124 makes contact with the appliance 110 over a surface area of at least 2 square millimeters, more preferably over a surface area of at least 2.8 square millimeters, and most preferably over a surface area of at least 3.5 square millimeters.

Second, the retaining member 124 and substrate 102 engage opposite facing sides of the appliance 110 thereby maintaining the appliance 110 in a fixed vertical position within the recess 104. In some embodiments, the retaining member 124 applies a gentle, continuous force that urges the appliance 110 toward the release surface 107 of the substrate 102 to help prevent the appliance 110 from wobbling when the packaged assembly 100 is handled and transported. Preferably, any force applied is sufficiently small so that the adhesive 114 located between the appliance 110 and the substrate 102 is not unduly compressed or otherwise distorted.

Preferably, the retaining member 124 exerts a compressive force on the appliance 110 having a component perpendicular to the release surface 107 ranging from 0 to 0.15 newtons (N), more preferably ranging from 0.02 to 0.12 N, and most preferably from 0.04 to 0.09 N. If present, it is preferable that these forces are small enough that the adhesive 114 does not extrude in lateral directions beyond the bonding base 112. In other embodiments, the retaining member 124 exerts essentially zero compressive force on the appliance 110 in directions perpendicular to the release surface 107 as to avoid any significant distortion of the adhesive 114.

Optionally, the retaining member 124 exerts gentle compressive forces on the appliance 110 in directions that are not perpendicular to the release surface 107 to further restrain lateral movement of the appliance 110. For example, the retaining member 124 may exert compressive forces on the appliance 110 having components parallel to the release surface 107. Preferably, any force components parallel to the release surface 107 are sufficiently small so that the retaining member 124 does not "grip" the appliance 110 and cause the appliance 110 and adhesive 114 to lift off prematurely from the release surface 107 when opening the lid 120.

In some embodiments, the retaining member 124 has a customized, pre-determined shape when relaxed that at least partially conforms to the labial surface of the appliance 110. By using a retaining member 124 having an outer surface that mechanically registers with at least a portion of the appliance 110, both the relative location and orientation of the appliance 110 can be precisely controlled. Alternatively, or in combination, the retaining member 124 can flexibly and resiliently deflect such that the retaining member 124 assumes the contours of the underlying labial surfaces of the appliance 110.

Optionally, the retaining member 124 is compressible. Various compressible materials can be used to construct the retaining member 124, including porous, polymeric open-celled and closed-cell foams, woven and non-woven materials. Preferred foam materials include ethylene propylene diene monomer and crosslinked polyethylene. In exemplary embodiments, the retaining member 124 has a compression deflection at 25 percent at a pressure of at most 14 kilopascals (2 pounds per square inch).

As another option, the retaining member 124 can include a friction enhancing coating which further hinders sliding movement between the retaining member 124 and the appliance 110.

FIG. 2 again illustrates the assembly 100, except with the lid 120 in a fully opened position. In this opened configuration, the retaining member 124 is removed from the vicinity of both the appliance 110 and the recess 104. During a bonding operation, a user applies a pair of tweezers, pliers, or other hand instrument to rapidly and conveniently extract the appliance 110 from the recess 104 and place the appliance 110 onto the patient's tooth. Advantageously, the appliance 110 is free of obstructions on all lateral sides, thereby facilitating the removal process.

While the contacting surfaces 123 are located on the tiewings 54 of the appliance 110, this need not be limiting. For example, other surfaces of the appliance 110 also non-parallel to the bottom surface 122 and release surface 107 include surfaces on the mesial and distal sides of the bracket body, between the bracket tiewings, and within the archwire slot. Any number of these surfaces may also contact the retaining member 124.

Figure 3A:
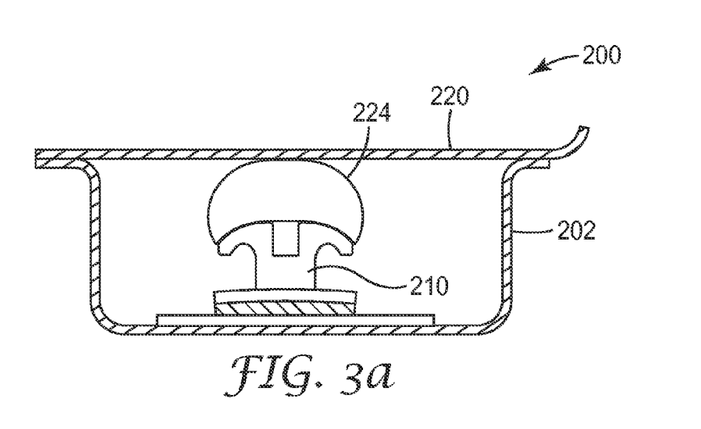
FIGS. 3a and 3b are side cross-sectional views of packaged orthodontic assemblies according to two other embodiments.

FIG. 3*a* shows an alternative orthodontic assembly 200, in which an appliance 210 is held in place by the combination of the substrate 202 and a retaining member 224 which is deformable but not volumetrically compressible (i.e. it does not decrease in volume). Retaining member 224 is an enclosed air-filled bladder that again conforms to the shape of the appliance when the lid 220 is closed. Like the retaining member 124, the retaining member 224 prevents undue movement of the appliance 210 relative to the substrate 202. In this case, the retaining member 224 contacts, and partially surrounds, a substantial portion of the labial face of the appliance 210.

Figure 3B:
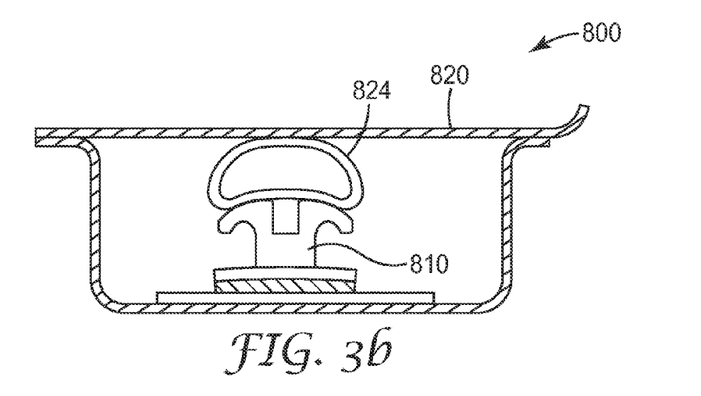

FIG. 3*b* shows a similar assembly 800 with a lid 820 that includes a retaining member 824 having a tubular cross-section. Because of its tubular shape, the retaining member 824 is capable of being deflected to conform to the labial surface of an underlying appliance 810 when the lid is closed. Retaining members that are hollow in general are also contemplated. Other aspects of the assemblies 200,800 are analogous to those described in assembly 100.

Figure 4:
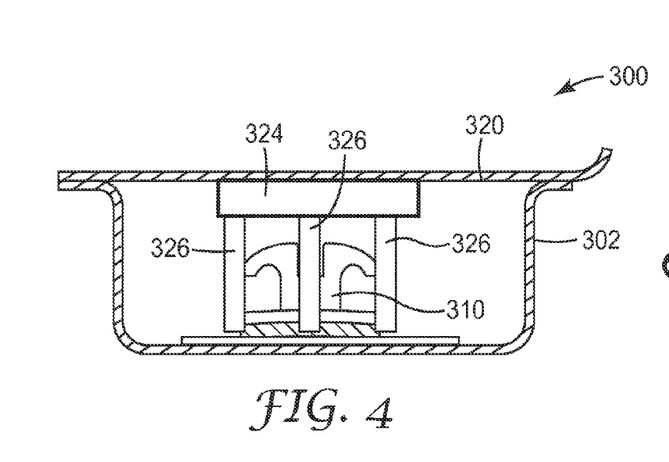
FIG. 4 is a side cross-sectional view of a packaged orthodontic assembly according to still another embodiment.
Figure 5:
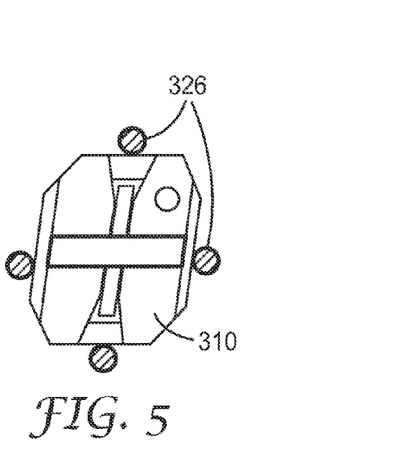
FIG. 5 is a fragmentary, cross-sectional plan view of the assembly of FIG. 4.

Still another embodiment is shown in FIGS. 4 and 5. These figures show two separate views of an assembly 300, in which a retaining member 324 having four discrete prongs 326 secures an appliance 310 within a substrate 302. The four prongs 326 extend from a lid 320 toward the release surface of the substrate 302 and rest against each of the occlusal, gingival, mesial, and distal sides of the appliance 310. Because the prongs 326 collectively surround the appliance 310 on at least two opposing sides, the appliance is again prevented from unduly shifting relative to the substrate 302 when the lid 320 is closed. If desired, the prongs 326 could be angled, bent, or curved to apply gentle compressive forces against the appliance 310 in the plane of the release surface thereby enhancing control over the lateral position and orientation of the appliance.

Figure 6:
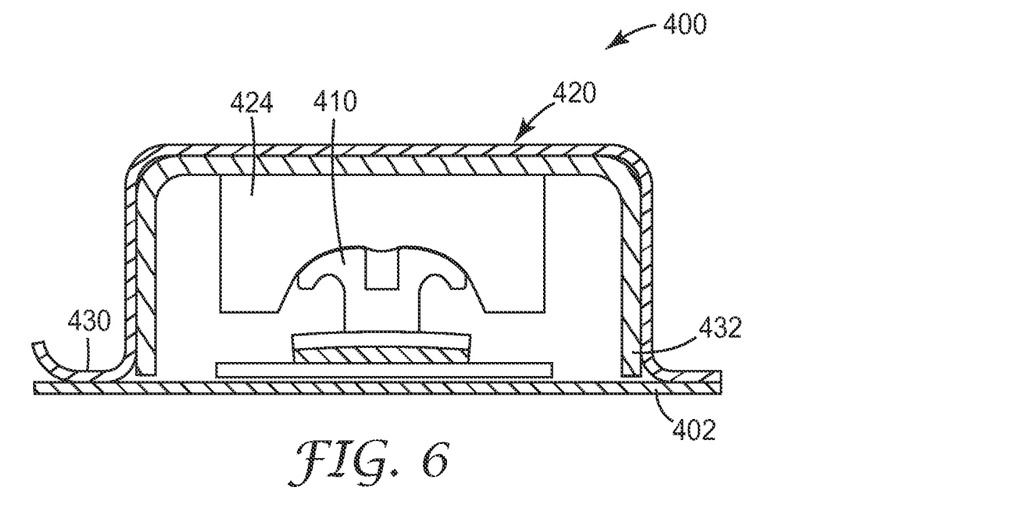
FIG. 6 is a side cross-sectional view of a packaged orthodontic assembly according to yet another embodiment.

The substrate of the orthodontic assembly need not be recessed. FIG. 6 shows an alternative assembly 400 having a substrate 402 that is rigid and generally planar in shape. In this configuration, a lid 420 having a pliable layer 430 and a rigid shell 432 extends over the substrate 402. The rigid shell 432 has a recess that receives an appliance 410 when the lid 420 is closed. The retaining member 424 is coupled to the underside of the rigid shell 432 and restricts undesirable movement of the appliance 410. The pliable layer 430 easily peels away from the substrate 402, allowing the rigid shell 432 to swing open and present the appliance 410.

The planar substrate further enhances the accessibility of the appliance 410 when the lid is opened. As another advantage, the overall size of the assembly can be made smaller, since it is no longer necessary to provide lateral space in the recess for hand instruments to access the appliance. Other options and advantages of using a recessed lid 420 are disclosed in U.S. Pat. No. 7,726,470 (Cinader et al.).

Figure 7:
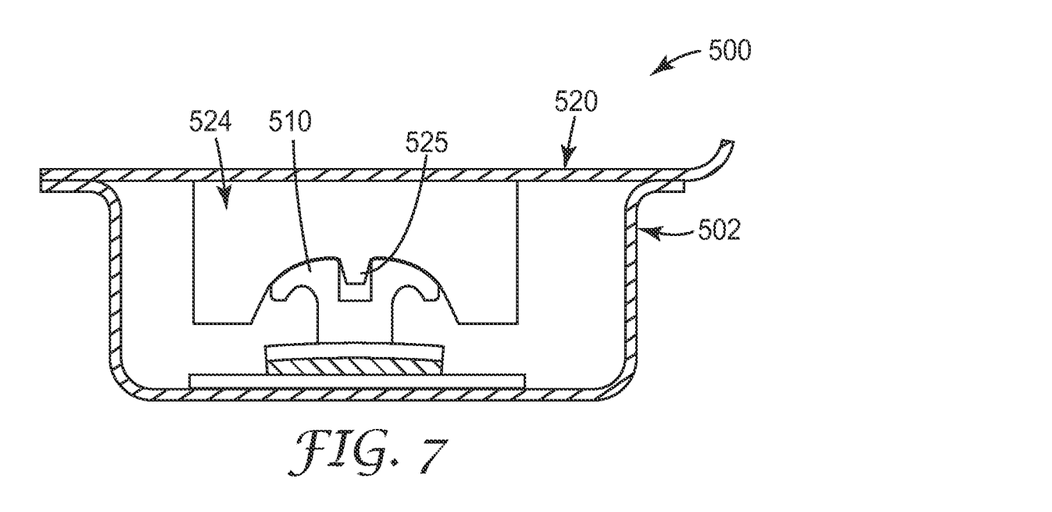
FIG. 7 is a side cross-sectional view of a packaged orthodontic assembly according to yet another embodiment.
Figure 8A:
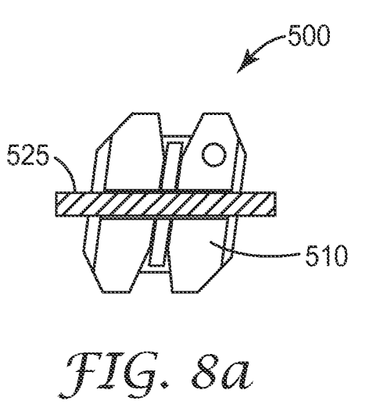
FIG. 8a is a fragmentary, cross-sectional plan view of the assembly of FIG. 7.

In other embodiments, the retaining member has one or more features that mechanically register with slots, grooves or other recesses located on the orthodontic appliance. For example, FIGS. 7 and 8a show an orthodontic assembly 500 having a substrate 502 and a lid 520 with a retaining member 524. The retaining member 524 has a blade-like protrusion 525 that is received into the archwire slot of an appliance 510 when the lid is closed.

Figure 8B:
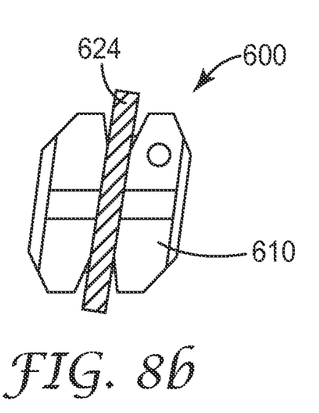
Figure 8C:
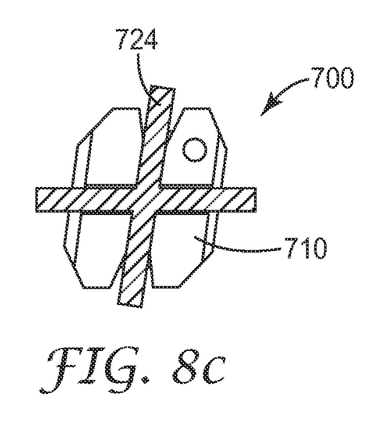

FIG. 8b shows an alternative assembly 600 in which a retaining member 624 is received in the vertical slot of an appliance 610. FIG. 8c shows yet another assembly 700 in which a generally cross-shaped retaining member 724 is received in both the vertical slot and the archwire slot of the appliance 710. The remainder of each of the assemblies of FIGS. 8b and 8c is the same as shown in FIG. 7. Each of the retaining members 524,624,724 engages its respective appliance 501,610,710 to prevent undesirable tipping, rotation, or sliding movement when the lid is closed, yet disengages from its respective appliance 510,610,710 to facilitate user access when the lid is opened. Optionally and as shown, the protrusions may be shortened or tapered to facilitate disengagement of the respective retaining members 524,624,724 from the respective appliances 510,610,710 when opening the lid.

Figure 2:
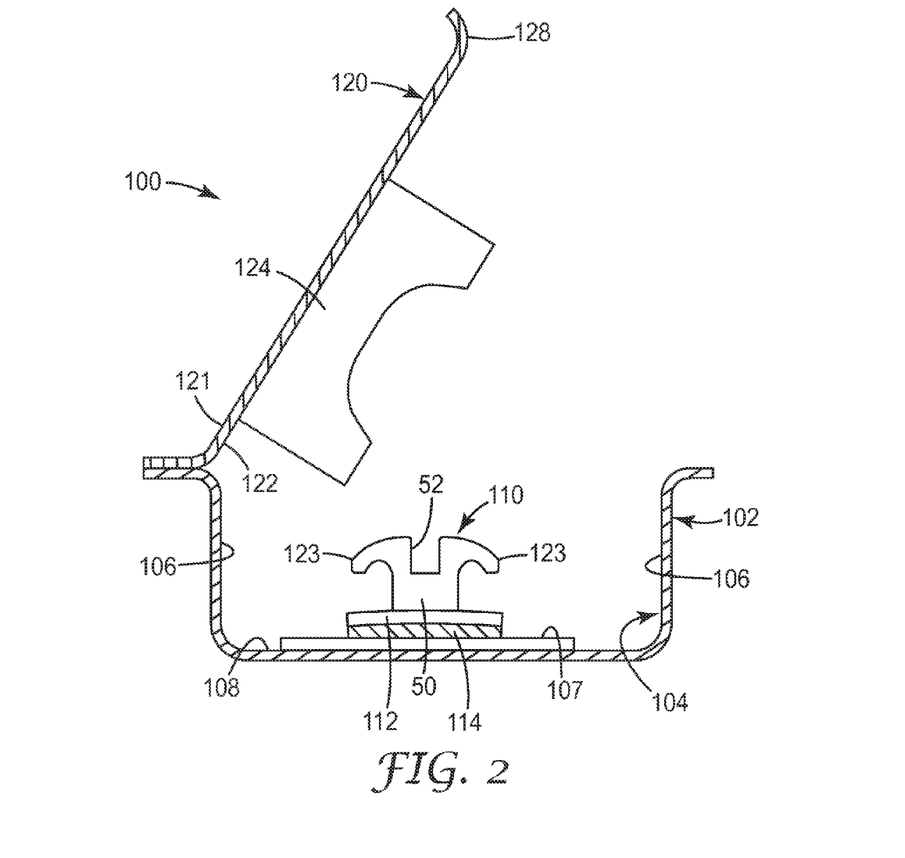
FIG. 2 is a side cross-sectional view of the assembly of FIG. 1 depicted in an opened configuration.

In an exemplary method of packaging an orthodontic assembly 100, the base of the appliance 110 in FIGS. 1-2 is initially coated with an orthodontic adhesive 114. The appliance 110 is then placed onto the substrate 102 such that the adhesive 114 releasably contacts the substrate 102. To seal the appliance 110 from light, moisture, and/or contaminants, the lid 120 is placed over both the appliance 110 and the substrate 102. When the lid 120 is in its closed position, the retaining member 124 at least partially surrounds the appliance to hinder relative sliding movement between the appliance and the substrate.

In an alternative method of packaging the assembly 100, the lid is inverted such that the bottom surface 122 is facing upwards. Then, the adhesive coated appliance 110 is placed upside down on the retaining member 124 of the lid 120. Finally, the lid 120 is held stationary while the substrate 102 is secured over the appliance 110 and lid 120. By closing the lid 120 in this manner, the adhesive 114 is pressed against the substrate 102, allowing the appliance 110 to be retained on the substrate 102 when the lid 120 is subsequently opened. Advantageously, this method allows a manufacturer to visually confirm that the retaining member 124 and the appliance 110 are precisely engaged with each other prior to sealing the lid 120.

It is understood that the above methods can also apply by analogy to assemblies 200, 300, 400, 500, and 800.

These assemblies and methods are advantageous to the orthodontic practitioner for several reasons.

First, the retaining member of the lid operates to securely retain the orthodontic appliance and pre-coated adhesive in a protective container during shipment and handling. In particular, the retaining member prevents the appliance from undue sliding motion relative to the lid during shipment and handling of the packaged orthodontic assembly. The retaining structure provided by the lid not only protects the appliance from impact but also helps preserve the shape and integrity of the unhardened adhesive pad, which is typically very delicate. The retaining member also conveniently disengages from the appliance when the lid is pulled back, allowing easy access by an orthodontic practitioner or assistant. The adhesive coated appliance may be conveniently plucked from the substrate using a pair of tweezers, or any other hand instrument suitable for this purpose.

Second, this configuration provides an answer to a persistent technical challenge associated with bulky appliances, such as buccal tubes, which apply uneven weight across the underlying adhesive pad. When these appliances are freshly coated with an adhesive and placed on a substrate, gravity often causes these appliances to "tip," resulting in an adhesive pad that is unduly thick on one side and unduly thin on the other. By mechanically registering with features on the appliance, the retaining member alleviates this undue tipping and preserves the uniformity of the adhesive pad on the base of the appliance.

Third, by securing the appliance on opposing sides, the retention mechanism provided by the retaining member alleviates the burden placed on the adhesive to retain the appliance on the substrate. As a result, the assembly can accommodate adhesives displaying a particularly wide range of tack and viscosity in the unhardened state. This is especially beneficial considering that filled orthodontic adhesives generally have viscosities that are shear-dependent and are susceptible to shift or distort within the container immediately after coating. These assemblies are also advantageous when exposed to elevated or reduced temperatures. While temperature fluctuations can affect the tack and/or viscosity of the coated adhesive, these effects are mitigated because the appliance is secured by the retaining structure.

Fourth, the use of retaining structure on the lid of a container also enables the use of non-porous release surfaces for retaining the pre-coated adhesive on the substrate. Previously, porous release surfaces were often preferred because of their effectiveness in preventing lateral "skating" of the adhesive along its surface. However, porous release surfaces also have the tendency to wick resin from the adhesive over time, leading to changes in adhesive texture. With the inclusion of a retaining member, it is possible to use non-porous, low-surface energy release surfaces that do not wick resin away from the pre-coated adhesive over time. Reduced wicking, in turn, provides for improved adhesive consistency during the shelf life of the pre-coated appliance.

All of the patents and patent applications mentioned above are hereby expressly incorporated by reference. The embodiments described above are illustrative of the present invention and other constructions are also possible. Accordingly, the present invention should not be deemed limited to the embodiments described in detail above and shown in the accompanying drawings, but instead only by a fair scope of the claims that follow along with their equivalents.

What is claimed is:

1. A packaged orthodontic assembly comprising:
    an orthodontic appliance having a base for attachment to a tooth surface;
    an adhesive extending across at least a portion of the base;
    a substrate having a release surface in contact with the adhesive;
    a lid coupled to the substrate and comprising a retaining member that contacts the appliance at a non-zero angle relative to the release surface to hinder relative sliding movement between the appliance and the release surface, the retaining member having a compression deflection of 25 percent at a pressure of at most 14 kilopascals, and wherein the retaining member exerts a compressive force on the appliance having a component perpendicular to the release surface ranging from 0 to 0.15 N.

2. The assembly of claim 1 wherein the substrate has a recess and the appliance is received in the recess.

3. The assembly of claim 1 wherein the lid has a recess and the appliance is received in the recess.

4. The assembly of claim 1, wherein at least a portion of the lid is releasably coupled to the substrate.

5. The assembly of claim 1, wherein the lid is pivotally coupled to the substrate.

6. The assembly of claim 1, wherein the retaining member comprises an open-celled polymeric foam.

7. The assembly of claim 6, wherein the foam comprises a polymer selected from the group consisting of: ethylene propylene diene monomer and crosslinked polyethylene.

8. The assembly of claim 1, and wherein the retaining member is at least partially complemental to the shape of the appliance and exerts a compressive force on the appliance having a component perpendicular to the release surface ranging from 0.2 to 0.12 N.

9. The assembly of claim 1, wherein the substrate further comprises a low-surface energy polymer coating and the release surface is located on the low-surface energy polymer coating.

10. The assembly of claim 1, wherein the substrate further comprises a porous polymeric foam and the release surface is located on the porous polymeric foam.

11. The assembly of claim 1, wherein the substrate further comprises a liner and the release surface is located on the liner.

12. The assembly of claim 1, wherein the retaining member makes contact with the appliance over a surface area of at least 3.5 square millimeters.

13. The assembly of claim 1, wherein the retaining member is coupled to or integral with the lid and extends outwardly from a surface of the lid.

14. The assembly of claim 1, wherein the retaining member exerts a compressive force on the appliance having a component perpendicular to the release surface ranging from 0.2 to 0.12 N.

15. A method of packaging an orthodontic appliance comprising:
coating a base of the appliance with an orthodontic adhesive;
placing the appliance on a substrate, wherein the adhesive contacts the substrate along a release surface of the substrate; and
placing a lid over both the appliance and the substrate, wherein the lid comprises a retaining member that has a compression deflection of 25 percent at a pressure of at most 14 kilopascals and at least partially surrounds the appliance while contacting the appliance at a non-zero angle relative to the release surface to hinder relative sliding movement between the appliance and the substrate.

16. The method of claim 15, wherein the retaining member has an outer surface with a shape that conforms to the shape of at least a portion of the appliance when the retaining member is relaxed.

17. A packaged orthodontic assembly comprising:
an orthodontic appliance having a base for attachment to a tooth surface;
an adhesive extending across at least a portion of the base;
a substrate having a recess, wherein the appliance is received in the recess; and
a lid coupled to the substrate and comprising a retaining member coupled to or integral with a surface of the lid and extending outwardly therefrom, the retaining member having a compression deflection of 25 percent at a pressure of at most 14 kilopascals, and wherein the retaining member exerts a compressive force on the appliance having a component perpendicular to a horizontal surface of the recess ranging from 0 to 0.15 N.

18. The packaged orthodontic assembly of claim 17, wherein the retaining member can flexibly and resiliently deflect such that a surface of the retaining member assumes the contours of a labial surface of the appliance.

19. The packaged orthodontic assembly of claim 17, wherein the retaining member includes a porous, compressible material.

20. The packaged orthodontic assembly of claim 17, wherein the retaining member exerts a compressive force on the appliance having a component perpendicular to a horizontal surface of the recess ranging from 0.2 to 0.12 N.

* * * * *